(12) United States Patent
Wang et al.

(10) Patent No.: US 6,670,175 B2
(45) Date of Patent: Dec. 30, 2003

(54) CRYOPRESERVATION BAG ASSEMBLY FOR MAMMALIAN CELL LINES

(75) Inventors: De Qian Wang, Concord, CA (US); Bruce Gardner, El Cerrito, CA (US); Rudiger Heidemann, Emeryville, CA (US); Mokhtar Mered, Orinda, CA (US); William H. Kelsey, Alameda, CA (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 63 days.

(21) Appl. No.: 10/143,194

(22) Filed: May 9, 2002

(65) Prior Publication Data

US 2002/0168759 A1 Nov. 14, 2002

Related U.S. Application Data

(60) Provisional application No. 60/289,924, filed on May 9, 2001, and provisional application No. 60/305,460, filed on Jul. 13, 2001.

(51) Int. Cl.[7] .................................................. C12M 1/00
(52) U.S. Cl. ........................ 435/307.1; 128/DIG. 24; 604/408; 604/409; 604/410; 604/415
(58) Field of Search ..................... 435/288.1, 288.2, 435/304.1, 304.2, 307.1, 309.1; 422/102; 128/DIG. 24; 604/408, 409, 410, 415

(56) References Cited

U.S. PATENT DOCUMENTS

| | | | | |
|---|---|---|---|---|
| 4,460,365 A | * | 7/1984 | Ganshirt et al. ............ 604/408 |
| 5,209,745 A | * | 5/1993 | Irr et al. ..................... 604/415 |
| 5,403,304 A | * | 4/1995 | Ishida ......................... 604/403 |
| 6,022,344 A | * | 2/2000 | Meijer et al. ............... 604/533 |

* cited by examiner

Primary Examiner—David A. Redding
(74) Attorney, Agent, or Firm—John W. Mahoney

(57) ABSTRACT

The invention is a novel cell freezing and storage bag assembly and method for using the assembly in the seed train expansion of mammalian cells. The bag is constructed principally of polytetrafluoroethylene fabric. The bag is designed to hold enough cells that a bioreactor can be inoculated directly. The bag is designed to be filled to a fraction of its maximum capacity so that the cell suspension has a very thin cross-section (less than about 10 millimeters). The bag design includes a transfer set that can be sterilely welded to the source of the mammalian cells. This sterile-weldable transfer set allows the bags to be filled quickly with minimal risk of contamination. In the method, once each bag is filled, it is sealed below the connection with the transfer set and the bag is cut "above" the new seal (on the same side of the seal as the transfer set). When a bioreactor is to be inoculated, the contents of the bag are drained via a sterile-weldable inoculation line. During freezing and storage, the inoculation line is protected from mechanical damage.

6 Claims, 6 Drawing Sheets

A detail of the cell freezing bag, showing a preferred embodiment of the spike port compartment, the inoculation line compartment, the inoculation line and its connection to the cell suspension compartment.

A preferred embodiment the sterile-weldable transfer set with attached bags.

A drawing of a preferred embodiment of a cell freezing bag, showing the various compartments.

A detail of the cell freezing bag, illustrating a preferred embodiment of the connection between the transfer set and the bag.

The preferred embodiment of the bag a) before filling, b) the filled and sealed bag, and c) the filled, sealed and cut bag.

A detail of the cell freezing bag, showing a preferred embodiment of the spike port compartment, the inoculation line compartment, the inoculation line and its connection to the cell suspension compartment.

A detail of the cell freezing bag, showing a preferred embodiment of the label compartment in cross-section. On the left the cell suspension compartment is unfilled (a, on the right it is filled (b.

CRYOPRESERVATION BAG ASSEMBLY FOR MAMMALIAN CELL LINES

CROSS REFERENCE TO RELATED APPLICATIONS

This application claims priority to Provisional Application No. 60/289924, filed on May 9, 2001, and to Provisional Application No. 60/305460 filed on Jul. 13, 2001.

FIELD OF THE INVENTION

The present invention relates to a flexible cryopreservation bag assembly and method for the freezing, storing, and transferring of mammalian cells. These mammalian cells are used to inoculate a bioreactor.

DESCRIPTION OF THE RELATED ART

Biotechnology products typically involve introducing some genetic modification into mammalian cells and then growing these cells in a bioreactor. These bioreactors are specially designed to allow the growth and maintenance of mammalian cells.

For the production of a drug from a specific line of genetically modified mammalian cells, a uniform cell source is needed every time a bioreactor is inoculated. This is the reason for a Manufacturer's Working Cell Bank (MWCB). An MWCB consists of many aliquots (portions) of a cell suspension, each containing the same type of cells and approximately the same number of cells. These aliquots are prepared on the same day and frozen at the same time. The aliquots are then kept at very cold temperatures (cryopreserved). For each run, one of these aliquots of cells is thawed to provide the same starting point as any other run with the same cells.

Successful inoculation of a bioreactor with mammalian cells requires a minimum cell density to achieve proper cell growth. If the cell density is below the minimum level, extended time requirements are required to achieve commercial cell growth levels, which adds expense to the process and the increases the opportunity for contaminants to enter the cell environment. If the cell density is too high, the nutrients in the media can be depleted, which results in reduced cell growth, and possibly death of the cell culture.

Under current practice, each aliquot in an MWCB has a volume of only 1–2 mL. This limited volume is necessitated by the need to freeze all cells in a rapid and uniform manner. Using existing technology, if large volumes are frozen, the diameter of the suspension will impact the rate of freezing and thawing of the cells, which can damage the cells and adversely impact bioreactor inoculation. The cell concentration in each aliquot is usually in the range of 1–20 million cells/mL. Production bioreactors typically contain tens of liters, hundreds of liters, or even greater volumes. Because of this dramatic difference in volume, a "seed train expansion" is used to increase the number of cells until there are enough to introduce into the production bioreactor. For all of the above reasons, the seed train expansion for a production campaign is a critical process step.

In typical production protocols, an aliquot of cells from the MWCB is thawed and the cells are cultured in small bottles (such as T-flasks). As the cells multiply, they are transferred to increasing numbers of small bottles. This increases the total number of cells without having too high or low a cell density. Once enough cells have accumulated, they are transferred into larger bottles (such as roller bottles or shake flasks). When another threshold is reached, the cells are transferred to an inoculation bioreactor. Finally, when enough cells have accumulated in the inoculation bioreactor, they are transferred to a production bioreactor. The seed train described is general practice for several mammalian cell lines and is widely used in commercial production and academia (Lindl and Bauer, 1989, Morgan and Darling, 1993). An overview of a commercial seed train expansion using T-flasks and spinner flasks is also given by Whitaker et al. 1998.

Typically, screw-top vials are used for the MWCB. The uses of screw-top vials necessitates unscrewing the vial caps prior to filling and screwing them back on after filling is a cumbersome manual operation. What is of greater concern is that while vials are open, the contents are subject to contamination. It is extremely important that no contamination is introduced into the vials.

Seed train expansions typically take about four to six weeks to complete under optimal conditions. Because of the large number of transfer steps, seed trains are labor intensive and are susceptible to contamination. Additionally, the environment in the small bottles and larger bottles are not well instrumented or controlled. Changes in pH and oxygen levels may lead to heterogeneity in the cells that are transferred to the production bioreactor. This in turn may lead to variability from one bioreactor run to another and ultimately can impact the quality of the drug being produced.

Each of the above-described risks to the preparation of a homogenous and uniformly viable cell suspension explains the need for improvements in this technology.

SUMMARY OF THE INVENTION

The invention is a novel cell freezing and storage bag assembly and method for using the assembly in the seed train expansion of mammalian cells. The bag is constructed principally of polytetrafluoroethylene fabric. The bag is designed to hold enough cells that a bioreactor can be inoculated directly. The bag is designed to be filled to a fraction of its maximum capacity so that the cell suspension has a very thin cross-section. The bag design includes a transfer set that can be sterilely welded to the source of the mammalian cells. This sterile-weldable transfer set allows the bags to be filled quickly with minimal risk of contamination. In the method, once each bag is filled, it is sealed below the connection with the transfer set and the bag is cut "above" the new seal (on the same side of the seal as the transfer set). When a bioreactor is to be inoculated, the contents of the bag are drained via a sterile-weldable inoculation line. During freezing and storage, the inoculation line is protected from mechanical damage.

BRIEF DESCRIPTION OF THE DRAWINGS

The accompanying drawings incorporated in and forming a part of the specification illustrate several aspects of the present inventions, and together with the description serve to explain the principles of the inventions. The components of the drawings are not necessarily to scale, emphasis instead being upon clearly illustrating principles of the present inventions.

DETAILED DESCRIPTION OF THE PREFERRED EMBODIMENTS

Figure 1:
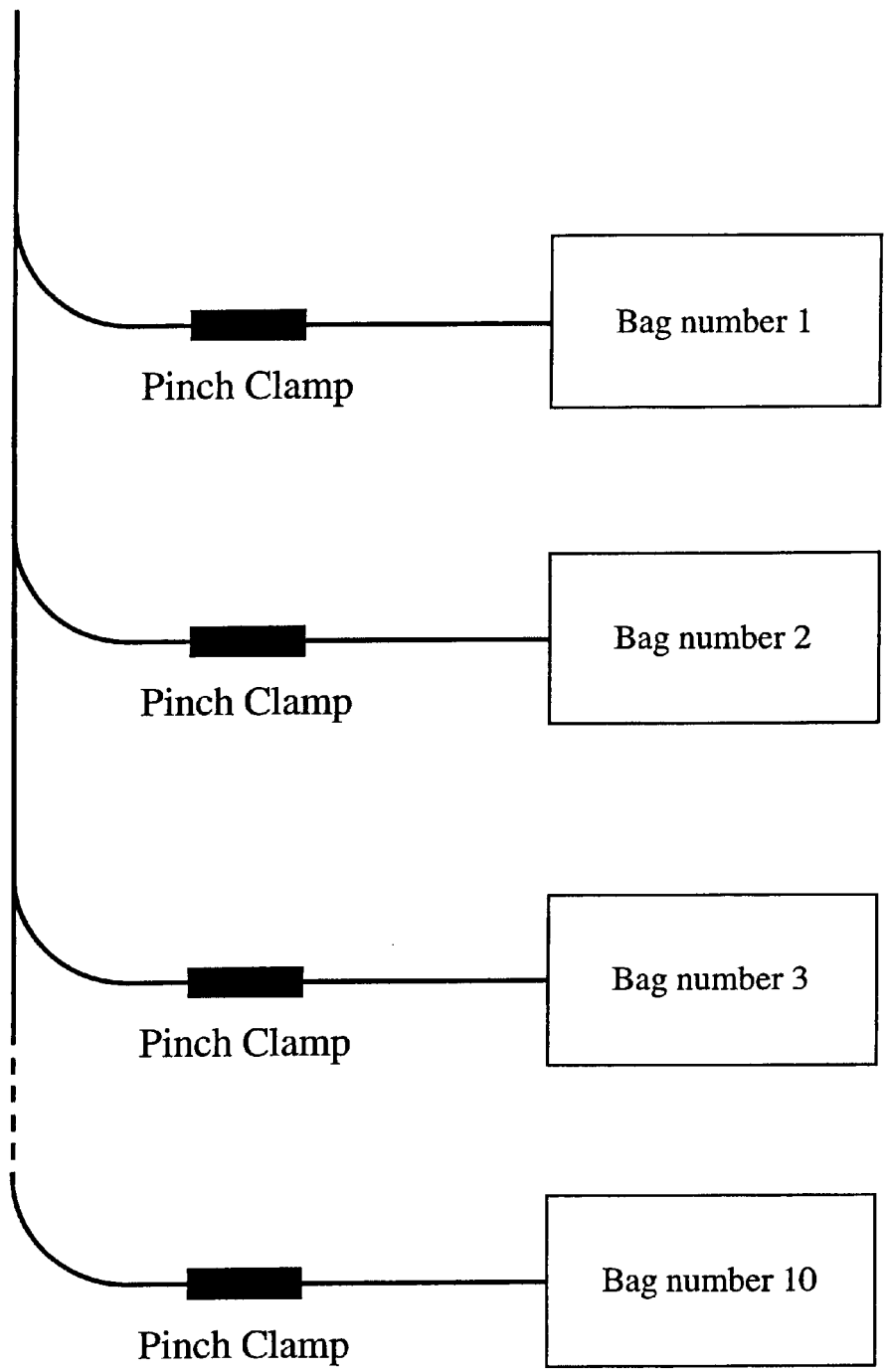
FIG. 1 is a drawing of a preferred embodiment for the sterile-weldable transfer set with attached bags.

Terms used in this specification are:

Bioreactor—A vessel containing a controlled environment for growing cells. Bioractors are also referred to as fermentors.

Polytetrafluoroethylene Fabric or Fabric—A flexible material that resembles a film or cloth made by any means from polytetrafluoroethylene. Common examples of Polytetrafluoroethylene fabric include Teflon® film.

Transfer set—A piece of flexible tubing, in some instances with one or more branches (referred to herein as "legs"), and used to connect the interior chamber of a storage bag with the exterior of the bag and or cell suspension source, and which permits the filling or draining of the contents of the bag.

Thin cross section—When cell freezing bags of the present invention are used, they will be placed on their side in a metal cassette (also referred to as a box or canister) in a substantially level orientation. The cell suspension thickness at any point within a bag should not exceed approximately 10 millimeters. If cell suspension thickness are substantially more than 10 millimeters, the cells adjacent to the bag surface will experience different freezing and thawing conditions than cells at the interior of the suspension, and may react differently over the course of freezing and thawing and when subsequently used in a bioreactor.

Cell freezing and storage bag assembly—The assembly includes the cell freezing bag and associated tubing, spike port and interconnects.

The invention is a cell freezing and storage bag assembly that supports a new method for the seed train expansion of mammalian cells. The bag is constructed principally of polytetrafluoroethylene. The bag is designed to hold enough cells that a bioreactor can be inoculated directly from its contents. The bag is designed to be filled to a fraction of its maximum capacity so that when placed on its side, the cell suspension has a very thin cross-section. The bag design includes a transfer set that can be sterilely welded to the source of the mammalian cells. This sterile-weldable transfer set allows the bags to be filled quickly with minimal risk of contamination. Once each bag is filled, it is sealed below the connection with the transfer set and the bag is cut "above" the new seal (on the same side of the seal as the transfer set). When a bioreactor is to be inoculated, the contents of the bag are drained via a sterile-weldable inoculation line. During freezing and storage, the inoculation line is protected from mechanical damage.

The cell freezing bag of the present invention is made of a polytetrafluoroethylene fabric in place of EVA (prior art bags). Polytetrafluoroethylene fabric is flexible at minus 180° C. and below. (Minus 180° C. is the temperature of liquid nitrogen. This is the practical minimum temperature for MWCB storage.) Because of its flexibility at low temperature, and in turn the reduced possibility of low temperature fracture, this fabric feature provides additional protection to the contents of the cell freezing bag during freezing, long-term storage, and thawing.

The cell freezing bag is designed to hold approximately 100 mL of cell suspension, 100 times the volume typically frozen in screw top vials. The cell densities are comparable for the new cell freezing bags and the vials that are currently used. Because of this volume difference, the bags can hold approximately 100 times more cells than the vials. A single cell freezing bag contains enough cells to allow direct inoculation of a bioreactor.

The cell suspension volumes to be frozen are a fraction of the cell freezing bag potential capacity. This limits the thickness of the cell suspension. Because the cell suspension is thin, heat transfer is rapid and the cells can be frozen uniformly at an optimal rate. Uniform freezing helps ensure the homogeneity of the cells.

The cell freezing bags are to be manufactured with an integral transfer set. This integral transfer set is composed of a length of flexible tubing, which in some applications may have one or more branches. These branches are sometime referred to as a leg or legs. When the bags are to be filled, the free end of the transfer set is sterilely welded to a length of tubing that is connected to the source of the cell suspension. This procedure virtually eliminates the chance of contamination when the bags are filled.

Each leg of the transfer set is connected to the cell freezing bag. Each leg has a pinch clamp or similar device to control the flow of cells to the attached cell freezing bag. The transfer set and attached bags are sterilized and delivered as a unit. For each bag the filling sequence is:

a) the pinch clamp on the attached transfer set leg is opened,
b) the cell suspension is pumped into the bag,
c) the pinch clamp is closed,
d) any air in the bag is pushed above the "sealing line" (a line below the connection with the transfer set)
e) the bag is sealed along the "sealing line", and
f) the bag is cut above the seal made in e), severing the connection between the bag and the transfer set.

If the cell suspension is pumped at a constant rate, the bags can be filled based on a fixed time interval. Once the bag is sealed and cut above the seal line, the transfer set is no longer attached to the bag. This eliminates one of the points of vulnerability during storage.

This invention uses an attached length of sterile-weldable tubing for draining the contents. This length of tubing is referred to as an inoculation line. One end of the inoculation line is attached to the body of the cell freezing bag. This attached end communicates freely with the compartment that contains the cell suspension. During storage, the inoculation line is protected from mechanical damage by being tightly enclosed in its own compartment. When the contents of the bag are to be used, the free end of the inoculation line is sterilely welded to a length of tubing that is connected to the inoculation bioreactor.

The invention is based on a new method for the seed train expansion of mammalian cells. Under this new method, the number of cells in each aliquot of the MWCB is increased. This reduces the extent to which cells must be multiplied in the seed train expansion. It is possible to increase the number of cells per aliquot somewhat by concentrating them. However it is more straightforward to increase the volume of each aliquot.

For the new method of seed train expansion of mammalian cells, the volume of the aliquot is increased to 100 mL. A dedicated inoculation bioreactor is directly inoculated by sterilely transferring the contents of the cell freezing bag to the bioreactor. This inoculation takes place without any intervening tissue culture-flasks, roller bottles, shake flasks, or comparable vessels. The initial volume of the culture in the dedicated inoculation bioreactor is 2 L, increasing to 15 L as the cell multiply (Heidemann et al, 2001).

It is not sufficient to use a larger vial with the same geometry as those used in current practice. When this geometry is scaled up, the larger cross-section results in longer freezing times and a significant thermal gradient from the outside of the vial to the center. This is at odds with the requirement for a homogeneous aliquot of cells for bioreactor inoculation. A bag-based design is used to provide a cross-section that is comparable in thickness to the cell freezing vials used in current practice. More specifically, the bag is filled to a fraction of its maximum capacity to give a very thin cross-section. The thin cross-section results in rapid cooling of the entire aliquot, with very little thermal gradient.

There are cell freezing bags on the market which accommodate the volumes described above (Vijayaraghhavan et al, 1998 and Regidor et al, 1999), however these bags have a number of limitations. The cell freezing bags currently available are constructed principally of ethylene vinyl acetate (EVA). EVA is brittle at the temperatures that cell suspensions are typically stored at. This results in the cell freezing bags being fragile from the time that the bag contents are reduced to storage temperatures to the time that the bag contents are starting to be thawed. This interval of vulnerability includes long term storage, which typically is measured in decades. Any cracking of the cell freezing bag in this interval of vulnerability is likely to result in contamination of the contents.

A second limitation of the currently available cell freezing bags is the extensive use of polyvinyl chloride (PVC) tubing for filling and draining the bags. PVC tubing is brittle at typical cell suspension storage temperatures, and the plasticizer used in making PVC materials is known to leach out of the plastic and into the surrounding media. Both of these limitations make PVC an undesirable choice for these cell freezing bags.

A third limitation of the cell freezing bags currently available is that they are emptied via a Luer-Lock or membrane-covered port. Again, this is a potential source of contamination.

FIG. 1. FIG. 1 shows the preferred embodiment for the sterile-weldable transfer set. The free end of the transfer set is sterile and weldable. In the preferred embodiment, all of the tubing in the transfer set is compatible with a sterile tubing welder. In some embodiments, some or all of the tubing other than the free end is not compatible with a sterile tubing welder.

In the preferred embodiment, there are 10 bags connected to the transfer set. In other embodiments, there are between 2 and 100 bags connected to the transfer set.

In this embodiment, the free end is on the same length of tubing that all of the legs are connected to. In other embodiments, there may be intervening joints or connectors between the free end and the legs.

In the preferred embodiment, the free end of the transfer set is sealed shut to avoid contamination. In other embodiments, the free end of the transfer set is not sealed shut, but instead is:

1. closed off by means of a clamp, or
2. closed off by means of a valve, or
3. a quick disconnect device, or
4. maintained in a sterile condition by means of secondary packaging.

In the preferred embodiment, the flow to each cell freezing bag is controlled by a single captive pinch valve. In other embodiments, the pinch clamps on the transfer set legs may not be captive, but may instead be applied to the tubing at the time of use. Additionally, in some embodiments, ball valves, gate valves, butterfly valves, or comparable inline flow control devices on the transfer set legs may be used in place of the pinch clamps.

In the preferred embodiment, the length from the free end to the start of the first leg is 10–15 centimeters. In other embodiments, this length can range from 1 centimeter to 1000 centimeters.

In the preferred embodiment, the length of each leg is 10–15 centimeters. In other embodiments, this length can be the same or vary from leg to leg within the range of 1 centimeter to 200 centimeters.

Figure 2:
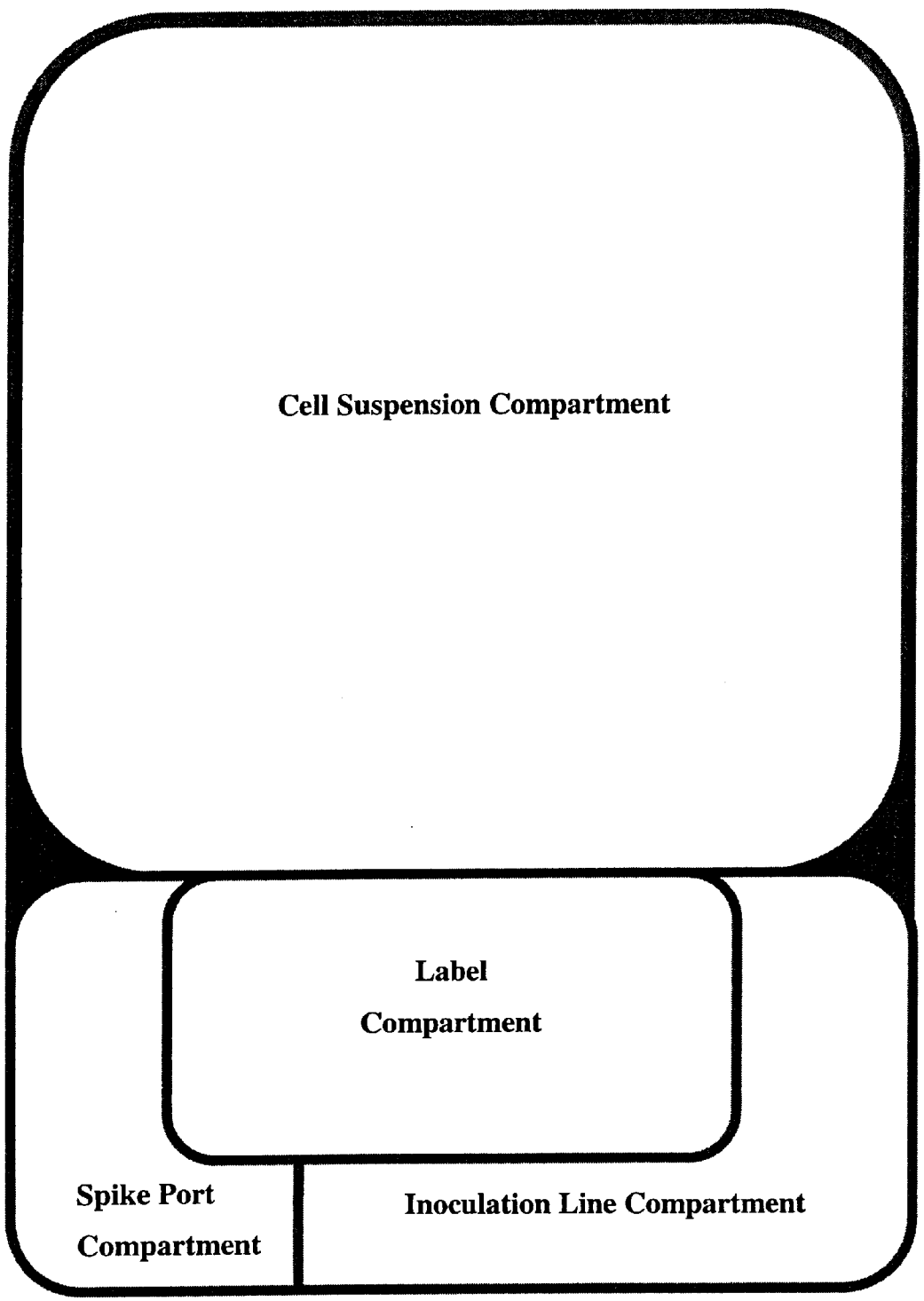
FIG. 2 is a drawing of a preferred embodiment of a cell freezing bag, showing the various compartments.

FIG. 2. FIG. 2 shows the preferred embodiment of the compartments in the cell freezing bag. When a cell freezing bag is filled with cell suspension, specifically it is the cell suspension compartment that is filled. This compartment is filled via the transfer set. The cell suspension remains in this compartment during freezing, storage and thawing. After thawing, the cell suspension is drained from this compartment via the inoculation line.

In the preferred embodiment, the capacity of the cell suspension compartment, when underfiled to maintain a suitably thin cross-section, is 100 milliliters. In other embodiments, the capacity of the cell suspension compartment may range from 2 milliliters to 5 liters.

In the preferred embodiment, the inoculation line compartment is show as being adjacent to both the cell suspension compartment and the label compartment. In other embodiments, the inoculation line compartment may be:

1. adjacent to the cell suspension compartment, but not adjacent to the label compartment, and/or
2. partially within the cell suspension compartment, or
3. entirely within the cell suspension compartment.

The inoculation line compartment will be further described in connection with FIG. 5.

The label compartment is accessed via a narrow slit. After the insertion of the label, the cell suspension compartment is filled. The increased thickness of the cell suspension compartment after filling obstructs the opening into the label compartment. This makes it unlikely that the label will slip out.

In some embodiments, there is no separate label compartment, the bag being labeled:

1. directly by ink or other pigment transfer (using a press, stamp, pen, marker, or printer), or
2. with an adhesive label, or
3. with a series of notches in the edge of the bag, or
4. with embossing of the bag material,
5. with a series of perforations of the bag material, or
6. with material included in cell suspension, or
7. with markings on the inoculation line.

Figure 3:
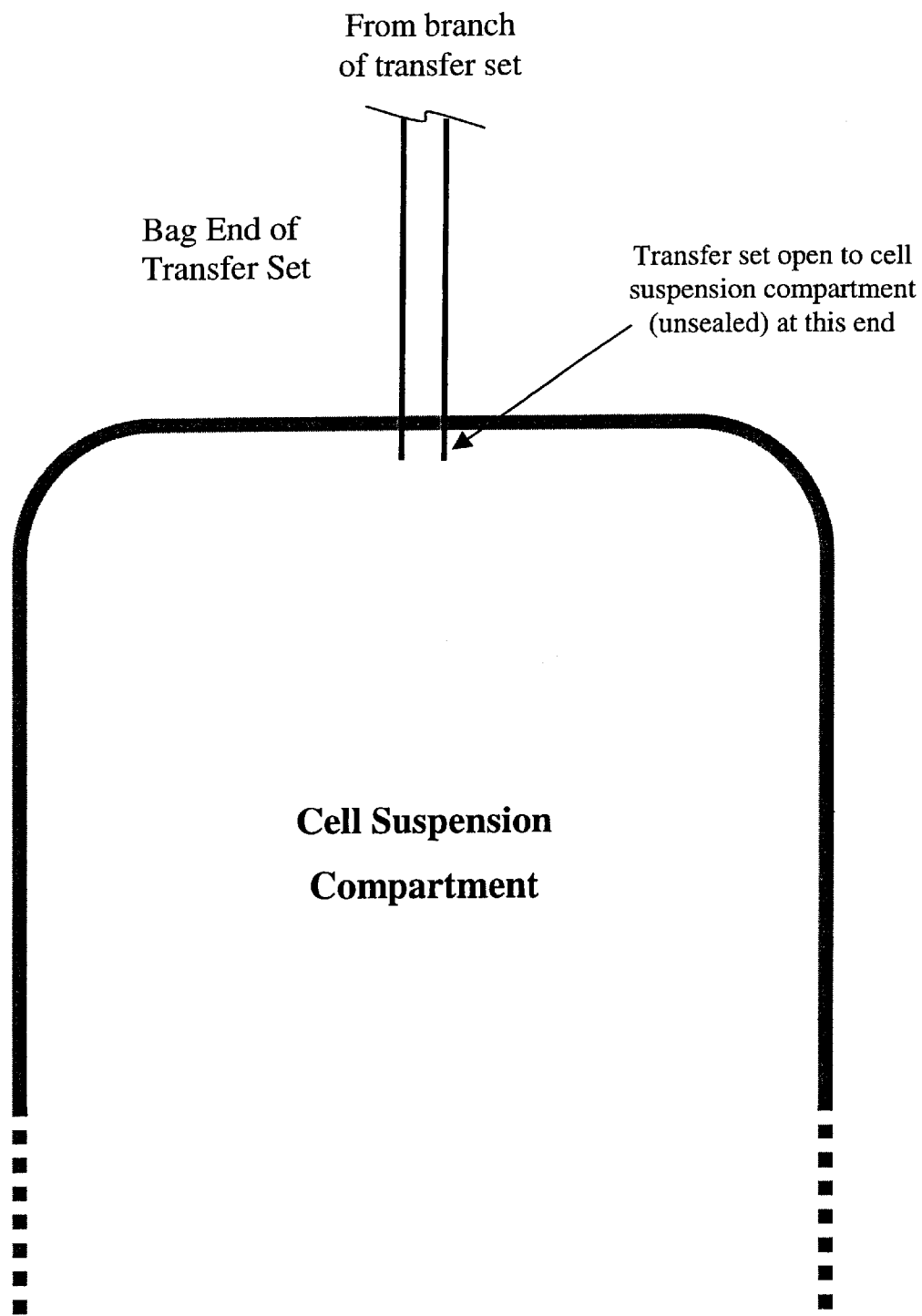
FIG. 3 is a detail of the cell freezing bag, illustrating a preferred embodiment of the connection between the transfer set and the bag.

FIG. 3. FIG. 3 shows the preferred embodiment of the connection between the bag end of the transfer set and the cell suspension compartment. In this embodiment, the end of the transfer set penetrates the seam of the cell suspension compartment. Additionally, in some embodiments, there may be a fitting that penetrates the seam of the cell suspension compartment and the transfer set is attached to this fitting.

The end of the transfer set that is inside the cell suspension compartment is open.

Figure 4:
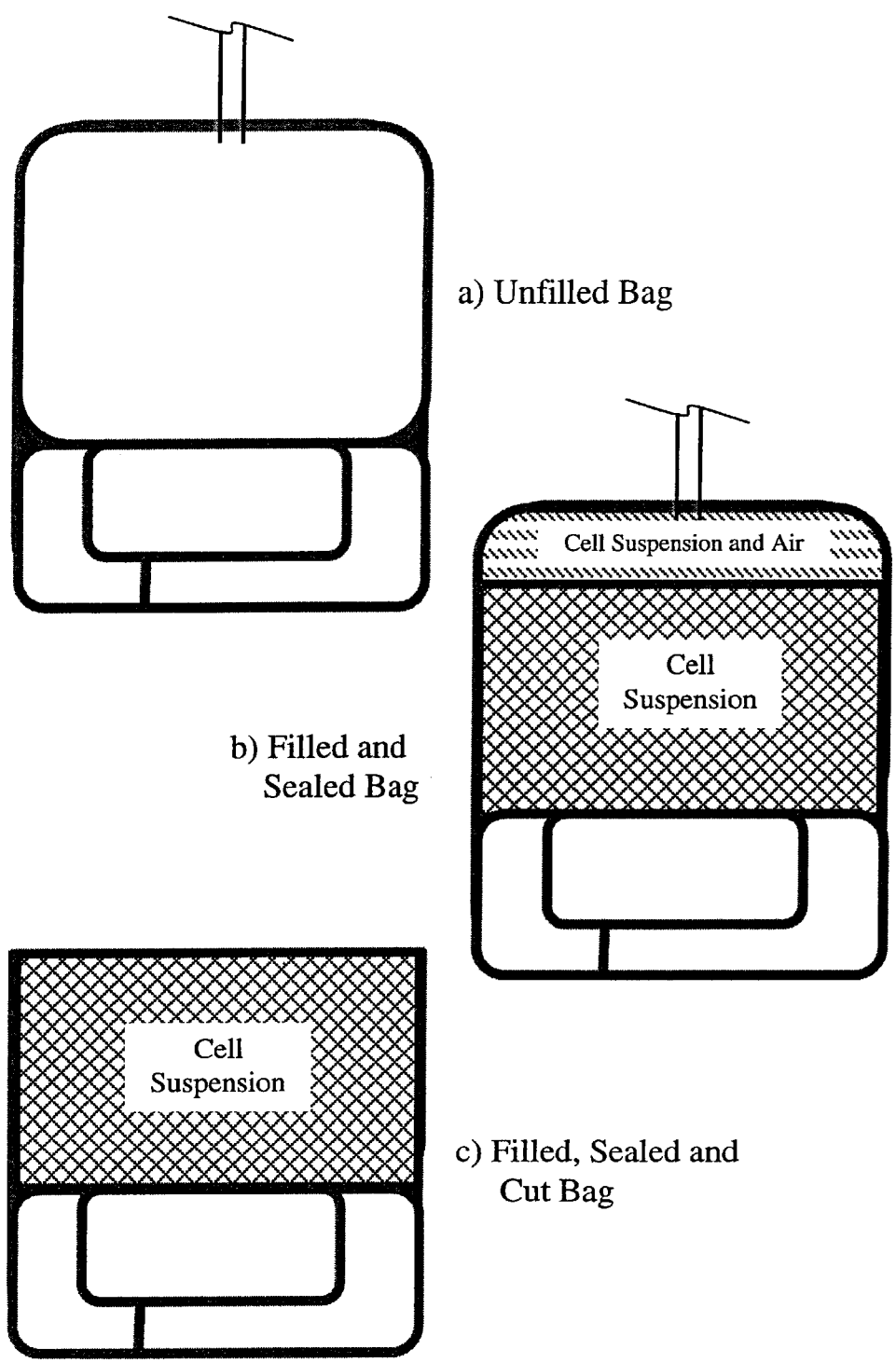
FIGS. 4a–c illustrates the preferred embodiment of the bag before filling, the filled and sealed bag, and the filled, sealed and cut bag.

FIG. 4. FIG. 4 illustrates the preferred embodiment of the bag before filling (a), the filled and sealed bag (b), and the filled, sealed and cut bag (c). The top drawing (a) shows the bag before it has been filled. Assuming the transfer set has already been attached to the cell source, the following steps take place between the top and middle drawings:

a) the pinch clamp on the attached transfer set leg is opened,
b) the cell suspension is pumped into the bag,
c) the pinch clamp is closed,
d) any air in the bag is pushed above the "sealing line", and
e) the bag is sealed along the "sealing line".

Between the middle (4(b)) and bottom drawings (4(c)), the bag is cut above the seal made in step e). This removes the transfer set from the portion of the bag to be frozen and stored. Also, the portion to be stored contains little or no air.

In the preferred embodiment, the sealing line is printed on the cell freezing bag directly by ink or other pigment transfer (using a press, stamp, pen, marker, or printer). In other embodiments, the sealing line is marked:

1. with embossing of the bag material, or
2. with an adhesive label, or
3. with material which is glued or welded to the bag, or
4. with one or more notches in the edge of the bag, or
5. with a series of perforations of the bag material at the edge of the bag.

Figure 5:
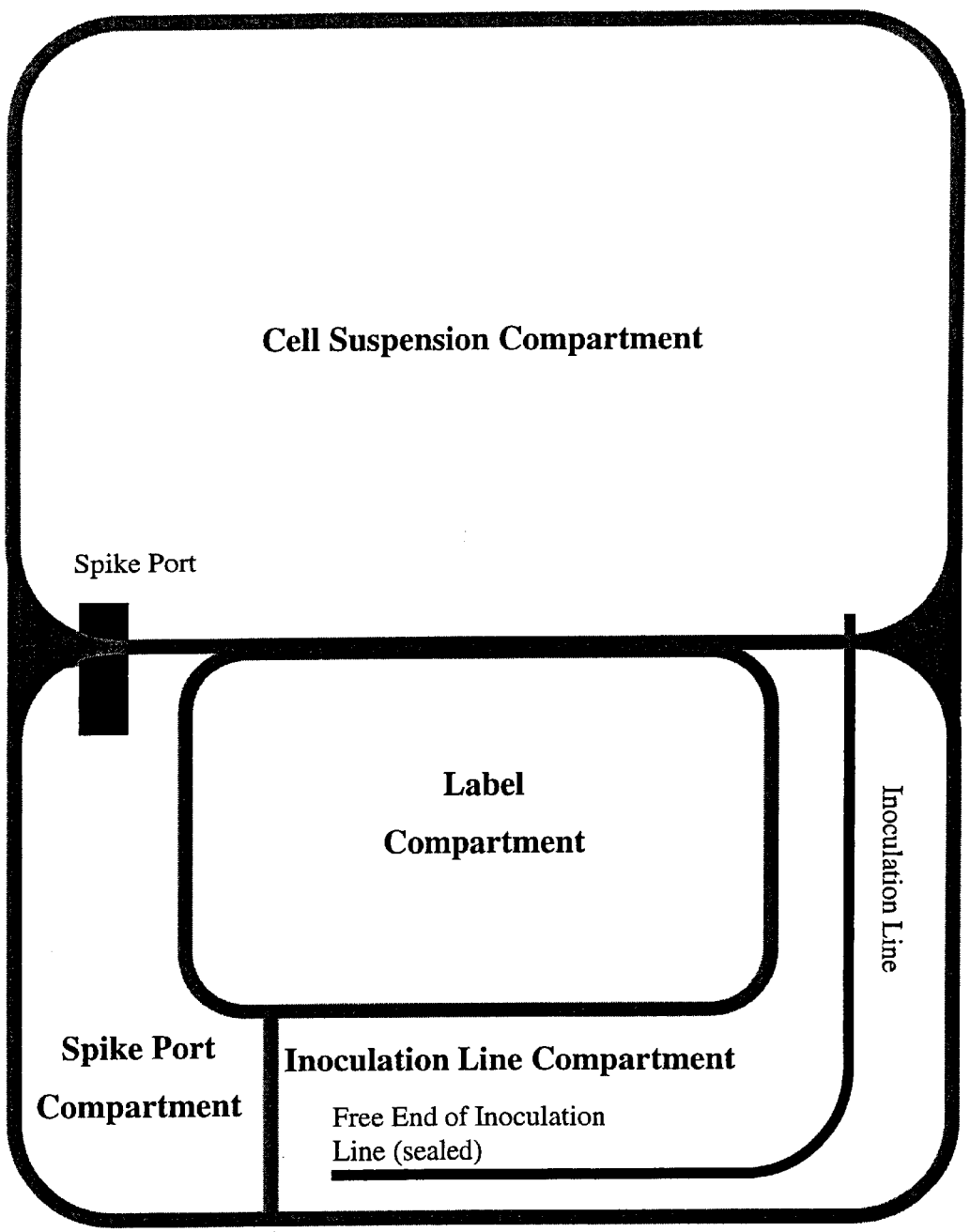
FIG. 5 is a detail of the cell freezing bag, showing a preferred embodiment of the spike port compartment, the inoculation line compartment, the inoculation line and its connection to the cell suspension compartment.
Figure 6:
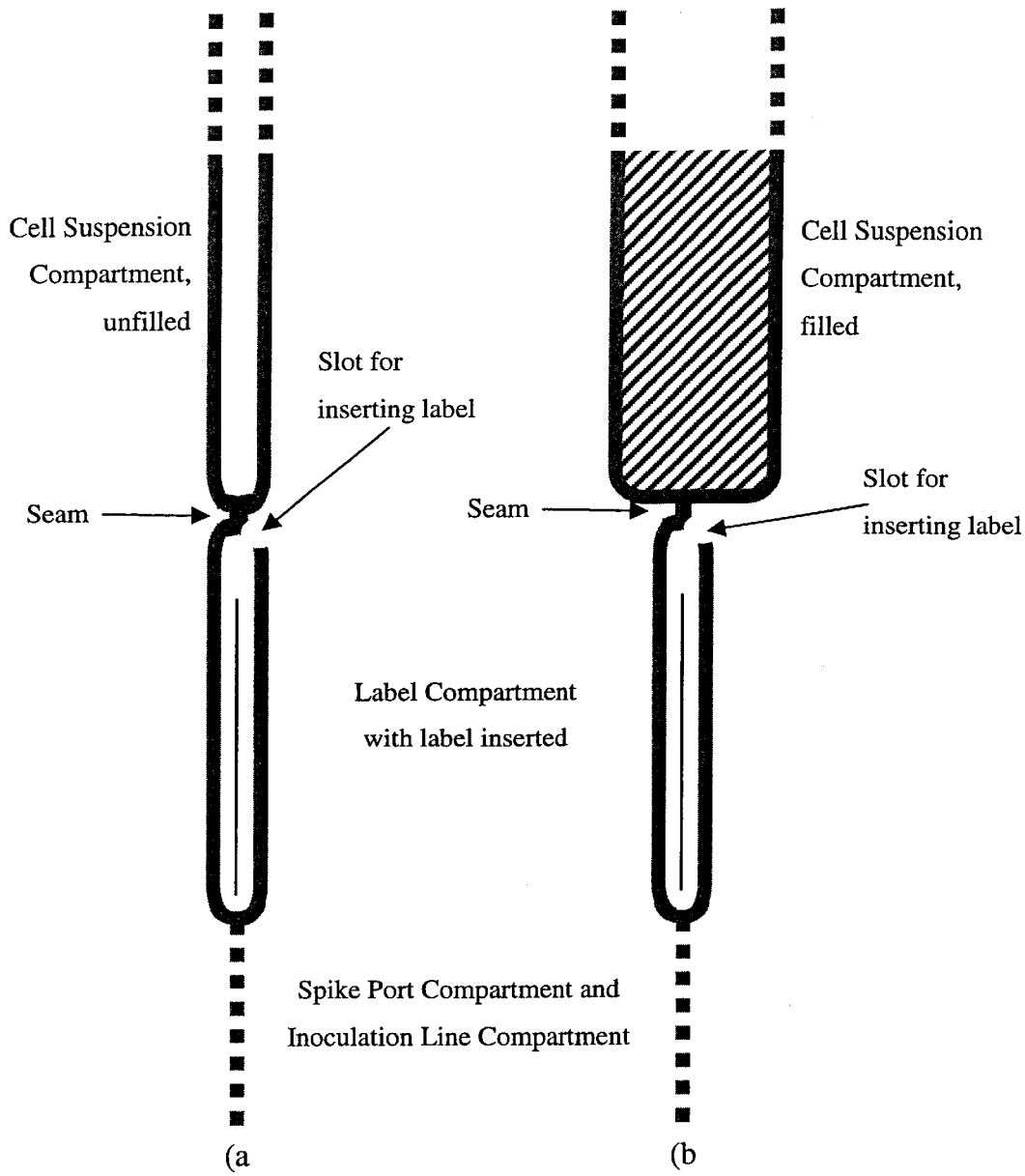
FIG. 6 is a detail of the cell freezing bag, showing a preferred embodiment of the label compartment in cross-section before and after the cell suspension compartment is filled.

FIG. 5. FIG. 5 shows the preferred embodiment of the spike port compartment, the inoculation line compartment, the inoculation line and its connection to the cell suspension compartment. In the preferred embodiment, the inoculation line compartment is sized to closely fit the inoculation line, providing it with protection against damage. By closely fitting the compartment to the inoculation line, only a limited volume of cell suspension is lost if there is any damage to the inoculation line. Additionally, in other embodiments, the inoculation line may be protected by the inclusion of packing material in the inoculation line compartment, the inclusion of stiffening material in the seams or surface of the inoculation line compartment, or the embedding of the inoculation line compartment in the cell suspension compartment.

In the preferred embodiment, the entire length of the inoculation is compatible with a sterile tubing welder. In some embodiments, some of the tubing other than the free end is not compatible with a sterile tubing welder.

In this embodiment, the inoculation tubing is a single length of tubing. In other embodiments, there may be intervening joints, elbows or other connectors in the inoculation tubing.

In the preferred embodiment, the length of the inoculation tubing within the inoculation tubing compartment is 10–20 centimeters. In other embodiments, the length of the tubing can range from 3 centimeters to 3 meters.

The end of the inoculation line that is inside the cell suspension compartment is open. In this embodiment, the end of the inoculation line penetrates the seam between the suspension compartment and the inoculation line compartment. Additionally, in some embodiments, there may be a fitting that penetrates the seam between the cell suspension compartment and the inoculation line compartment, and the transfer set is attached to this fitting.

In the preferred embodiment, the inoculation line has one ninety degree bends within the inoculation line compartment. Additionally, in other embodiments, the inoculation line may:

1. have no bends, or
2. have a number of 90° bends other that 1, but between one and twenty, or
3. have one to twenty bends at angles greater or less than 90°, or
4. have one to twenty bends at a combination of angles, or
5. form a spiral. (Note that a spiral line may be more difficult to use in conjunction with a sterile tubing welder.)

In the preferred embodiment, the free end of the inoculation line is sealed shut to avoid contamination and to reduce the likelihood that the cell suspension will migrate into the inoculation line prior to the bag being emptied. Additionally, in some embodiments, the free end of the inoculation line is not sealed shut, but instead is closed off by means of:

1. a ball valve, gate valve, butterfly valve, or comparable inline flow control devices incorporated by the manufacturer, or
2. a ball valve, gate valve, butterfly valve, or comparable inline flow control devices incorporated added by the user, or
3. a clamp that is applied by the manufacturer, or
4. a clamp that is applied by the user, or
5. a quick disconnect device with built-in valving, or
6. a quick disconnect device that is capped by the manufacturer, or
7. a quick disconnect device that is capped by the user.

FIG. 5 also illustrates the spike port compartment. In the event that the inoculation line is damaged, it will be possible to drain the bag by means of the spike port. Since the spike port is in its own compartment, it can be accessed without loosing additional cell suspension from the inoculation line.

What is claimed is:

1. A manufacturer's working cell bank cryopreservation bag assembly comprising:

a polytetrafluoroethylene bag, the bag comprising four separate and sealed compartments, said compartments comprising a cell suspension compartment, a spike port compartment, an inoculation line compartment and a label compartment;

a first length of non-PVC tubing that can be used for sterile docking before cryopreservation and connected to and communicating with one of the sealed compartments;

a second length of non-PVC tubing that can be used for sterile docking after cryopreservation and connected to and communicating with one of the sealed compartments, said second length of tubing being minus 180 degrees centigrade temperature resistant; and a spike port having means to export cells from one of the compartments.

2. The cryopreservation bag assembly of claim 1, in which the cell suspension compartment comprises a leakproof attachment means joining said first length of tubing to said cell suspension compartment, and through which cells may be transferred into said compartment.

3. The cryopreservation bag assembly of claim 1, in which the inoculation line compartment comprises a leakproof minus 180 degree centigrade temperature resistant attachment means joining said second length of tubing to said cell suspension compartment and through which cells may be transferred out of said compartment.

4. The cryopreservation bag assembly of claim 3, in which the second length of tubing is contained within the inoculation line compartment.

5. The cryopreservation bag assembly of claim 1, in which the spike port is enclosed within the spike port compartment.

6. The cryopreservation bag assembly of claim 1, in which the label compartment comprises an access slot configured to allow insertion of a label into said label compartment.

* * * * *